United States Patent
Eccleston et al.

(10) Patent No.: US 10,768,182 B2
(45) Date of Patent: Sep. 8, 2020

(54) METHOD FOR DETECTING NUCLEOSOMES CONTAINING HISTONE MODIFICATIONS AND VARIANTS

(71) Applicant: BELGIAN VOLITION SPRL, Isnes (BE)

(72) Inventors: Mark Edward Eccleston, Isnes (BE); Jacob Vincent Micallef, Isnes (BE)

(73) Assignee: Belgian Volition SPRL, Isnes (BE)

( * ) Notice: Subject to any disclaimer, the term of this patent is extended or adjusted under 35 U.S.C. 154(b) by 74 days.

(21) Appl. No.: 15/768,981

(22) PCT Filed: Oct. 21, 2016

(86) PCT No.: PCT/GB2016/053288
§ 371 (c)(1),
(2) Date: Apr. 17, 2018

(87) PCT Pub. No.: WO2017/068359
PCT Pub. Date: Apr. 27, 2017

(65) Prior Publication Data
US 2019/0064183 A1    Feb. 28, 2019

(30) Foreign Application Priority Data

Oct. 21, 2015 (GB) .................................. 1518674.5

(51) Int. Cl.
*G01N 33/68* (2006.01)
*G01N 33/574* (2006.01)

(52) U.S. Cl.
CPC ... *G01N 33/6875* (2013.01); *G01N 33/57488* (2013.01); *G01N 33/6893* (2013.01)

(58) Field of Classification Search
None
See application file for complete search history.

(56) References Cited

U.S. PATENT DOCUMENTS

2013/0230858 A1    9/2013 Cantor et al.

FOREIGN PATENT DOCUMENTS

| WO | WO-2011/150974 A1 | 12/2011 |
| WO | WO-2013/030577 A1 | 3/2013 |
| WO | WO-2013/030579 A1 | 3/2013 |
| WO | WO-2014/131841 A1 | 9/2014 |

OTHER PUBLICATIONS

Eggena et al. (J. Autoimmunity 2000 vol. 14, p. 83-97 (Year: 2000).*
Fujiya et al., "Nucleosomal DNA hypermethylation detected in sera of colon cancer patients as a marker of cancer surveillance", Digest Dis. Week Abs., 2003, Abstract No. W1331. (2 pages).
Holdenrieder et al., "Nucleosomes in Serum of Patients With Benign and Malignant Diseases", Int. J. Cancer, 2001, 95:114-120.
Holdenrieder et al., "Clinical use of circulating nucleosomes", Critical Reviews in Clinical Laboratory Sciences United States, 2009, 46(1):1-24.
Scaffidi, Paola, "Histone H1 alterations in cancer", Biochemica et Biophysica Acta, 2016, 1859(3):533-539.
Izzo & Schneider, "The role of linker histone H1 modications in the regulation of gene expression and chromatin dynamics", BBA Gene Regulatory Mechanisms, 2016, 1859:486-495.
Gabler et al., "Extranuclear detection of histones and nucleosomes in activated human lymphoblasts as an early event in apoptosis", Annals of the Rheumatic Diseases, 2004, 63(9):1135-1144.
Hergeth et al., "The H1 linker histones: multifunctional proteins beyond the nucleosomal core particle", EMBO Reports, 2015, 16(11):1439-1453.
Sakamoto et al., (2010) "Immunoprecipitation of nucleosomal DNA is a novel procedure to improve the sensitivity of serum screening for the p16 hypermethylation associated with colon cancer", The International Journal of Cancer Epidemiology, Detection, and Prevention, vol. 34, pp. 194-199.

* cited by examiner

*Primary Examiner* — Changhwa J Cheu
(74) *Attorney, Agent, or Firm* — McDermott, Will & Emery LLP; Judy M. Mohr

(57) ABSTRACT

The present invention relates to a method for detecting and measuring the presence of cell free mono-nucleosomes and oligo-nucleosomes that contain histone H1 or a histone H1 modification, variant or isoform, and the use of such measurements for the detection and diagnosis of disease.

8 Claims, No Drawings

METHOD FOR DETECTING NUCLEOSOMES CONTAINING HISTONE MODIFICATIONS AND VARIANTS

CROSS-REFERENCE TO RELATED APPLICATIONS

This application is a U.S. National Stage Application of PCT/GB2016/053288, filed Oct. 21, 2016, which claims the benefit of and priority to GB Patent Application No. GB 1518674.5 filed Oct. 21, 2015, the entire contents of each of which is incorporated herein by reference.

FIELD OF THE INVENTION

The invention relates to a cell free nucleosome comprising a histone H1 protein or a histone H1 modification, variant or isoform for use as a biomarker for the diagnosis of cancer, cardiomyopathy, systemic lupus erythematosus, colitis, chronic obstructive pulmonary disorder, Crohn's disease and rheumatoid arthritis. The invention further relates to methods for detecting and measuring the presence of mono-nucleosomes and oligo-nucleosomes and nucleosomes that contain histone H1 or a histone H1 modification, variant or isoform and the use of such measurements for the detection and diagnosis of disease. The invention also relates to a method of identifying histone H1 modification and variant biomarkers for the detection and diagnosis of disease and to biomarkers identified by said method.

BACKGROUND OF THE INVENTION

The human body comprises several hundred cell types. All of these cell types contain the same genome but have widely different phenotypes and different functions in the body. This phenotypic diversity is due to the differential expression of the genome in different cell types. The control of differential gene expression is not entirely understood but the basic mechanisms include gene regulation by a number of interconnected epigenetic signals associated with the gene, including control of the chromatin packing as euchromatin or heterochromatin, control of nucleosome positioning and nuclease accessible sites, methylation of DNA and variation in the structure of the nucleosomes around which the DNA is wrapped.

The nucleosome is the basic unit of chromatin structure and consists of a protein complex of eight highly conserved core histones (comprising a pair of each of the histones H2A, H2B, H3, and H4). Around this complex are wrapped approximately 146 base pairs of DNA. Another histone, H1 or H5, acts as a linker and is involved in chromatin compaction. The DNA is wound around consecutive nucleosomes in a structure often said to resemble "beads on a string" and this forms the basic structure of open or euchromatin. In compacted or heterochromatin this string is coiled and super coiled into a closed and complex structure (Herranz and Esteller, 2007).

The structure of nucleosomes can vary by Post Transcriptional Modification (PTM) of histone proteins and by the inclusion of variant histone proteins. PTM of histone proteins typically include acetylation, methylation or ubiquitination of lysine residues as well as methylation of arginine residues and phosphorylation of serine residues and many others. Histone modifications are known to be involved in epigenetic regulation of gene expression (Herranz and Esteller, 2007). The structure of the nucleosome can also vary by the inclusion of alternative histone isoforms or variants which are different gene or splice products and have different amino acid sequences. Histone variants can be classed into a number of families which are subdivided into individual types. The nucleotide sequences of a large number of histone variants are known and publicly available for example in the National Human Genome Research Institute NHGRI Histone DataBase (Marino-Ramirez, L et al. The Histone Database: an integrated resource for histones and histone fold-containing proteins. Database Vol. 2011, Article ID bar048; and http://genome.nhgri.nih.gov/histones/complete.shtml), the GenBank (NIH genetic sequence) DataBase, the EMBL Nucleotide Sequence Database and the DNA Data Bank of Japan (DDBJ).

Normal cell turnover in adult humans involves the creation by cell division of some $10^{11}$ cells daily and the death of a similar number, mainly by apoptosis. During the cell death process chromatin is broken down into chromatin fragments including mononucleosomes and oligonucleosomes some of which may be released into the circulation or other body fluids as cell free nucleosomes. Under normal conditions the level of circulating nucleosomes found in healthy subjects is reported to be low. Elevated levels are found in subjects with a variety of conditions including many cancers, auto-immune diseases, inflammatory conditions, stroke and myocardial infarction (Holdenreider & Stieber, 2009). The DNA associated with cell free nucleosomes is cell free DNA.

Mononucleosomes and oligonucleosomes can be detected by Enzyme-Linked ImmunoSorbant Assay (ELISA) and several methods have been reported (Salgame et al, 1997; Holdenrieder et al, 2001; van Nieuwenhuijze et al, 2003). These assays typically employ an anti-histone antibody (for example anti-H2B, anti-H3 or anti-H1, H2A, H2B, H3 and H4) as capture antibody and an anti-DNA or anti-H2A-H2B-DNA complex antibody as detection antibody. Using these assays workers in the field report that the level of nucleosomes in serum is higher (by up to an order of magnitude) than in plasma samples taken from the same patients. This is also true for serum and plasma measurements of DNA made by PCR (Holdenrieder et al, 2005). The reason for this is not known but the authors speculate that it may be due to additional release of DNA during the clotting process. However, we have found that the results of nucleosome ELISA assays of the current art do not agree with each other. Furthermore, although most circulating DNA in serum or plasma is reported to exist as mono-nucleosomes and oligo-nucleosomes (Holdenrieder et al, 2001), measured levels of nucleosomes and DNA in serum or plasma do not agree well. The correlation coefficient between ELISA results for circulating cell free nucleosomes levels and circulating DNA levels as measured by real time PCR (Polymerase Chain Reaction) has been reported to be r=0.531 in serum and r=0.350 in plasma (Holdenrieder et al, 2005).

Current nucleosome ELISA methods are used in cell culture, primarily as a method to detect apoptosis (Salgame et al, 1997; Holdenrieder et al, 2001; van Nieuwenhuijze et al, 2003), and are also used for the measurement of circulating cell free nucleosomes in serum and plasma (Holdenrieder et al, 2001). Cell free serum and plasma nucleosome levels released into the circulation by dying cells have been measured by ELISA methods in studies of a number of different cancers to evaluate their use as a potential biomarker (Holdenrieder et al, 2001). Mean circulating nucleosome levels are reported to be high in most, but not all, cancers studied. The highest circulating nucleosome levels were observed in lung cancer subjects. The lowest levels were observed in prostate cancer, which were within the normal range of healthy subjects. However, patients with malignant tumours are reported to have serum nucleosome concentrations that varied considerably and some patients with advanced tumour disease were found to have low circulating nucleosome levels, within the range measured for healthy subjects (Holdenrieder et al, 2001). Because of this and the variety of non-cancer causes of raised nucleosome levels, circulating nucleosome levels are not used clinically as a biomarker of cancer (Holdenrieder and Stieber, 2009).

ELISA methods for the detection of histone PTMs are also known in the art. ELISA methods for PTM detection in free histone proteins (not attached to other histones and DNA in a nucleosome complex) are used for the detection of PTMs in histones extracted, usually by acid extraction, from cell lysates. Immunoassay for the detection of PTMs in circulating cell free nucleosomes has been reported (WO 2005/019826). A method for ELISA detection of histone PTMs in purified nucleosomes directly coated to microtitre wells has also been reported (Dai et al, 2011). In this method nucleosomes obtained by digestion of chromatin extracts from cultured cells are coated directly to microtitre wells and reacted with anti-PTM antibodies. It will be clear to those skilled in the art that this method requires relatively pure nucleosome samples and is not suitable for the direct measurement of histone PTMs in complex biological media such as blood or serum.

A modified chromatin immunoprecipitation (ChIP) method for the detection of a histone PTM (H3K9Me, histone H3 monomethylated at lysine residue K9) in cell free nucleosomes associated with a particular DNA sequence has been reported in plasma. The level of sequence specific histone methylation was reported to be independent of the concentration of circulating nucleosomes (Deligezer et al, 2008).

In addition to the epigenetic signaling mediated by nucleosome position and nucleosome structure (in terms of both constituent histone protein variant and PTM structures), control of gene expression in cells is also mediated by modifications to DNA nucleotides including the cytosine methylation status of DNA. It has been known in the art for some time that DNA may be methylated at the 5 position of cytosine nucleotides to form 5-methylcytosine. Methylated DNA in the form of 5-methylcytosine is reported to occur at positions in the DNA sequence where a cytosine nucleotide occurs next to a guanine nucleotide. These positions are termed "CpG" for shorthand. It is reported that more than 70% of CpG positions are methylated in vertebrates (Pennings et al, 2005). Regions of the genome that contain a high proportion of CpG sites are often termed "CpG islands", and approximately 60% of human gene promoter sequences are associated with such CpG islands (Rodriguez-Paredes and Esteller, 2011). In active genes these CpG islands are generally hypomethylated. Methylation of gene promoter sequences is associated with stable gene inactivation. DNA methylation also commonly occurs in repetitive elements including Alu repetitive elements and long interspersed nucleotide elements (Herranz and Estellar, 2007; Allen et al, 2004).

Histone variants (also known as histone isoforms) are also known to be epigenetic regulators of gene expression (Herranz and Esteller, 2007). Histone variants have been studied in vivo and in vitro using a variety of techniques including knock-down studies of the gene encoding a particular variant (for example using RNAi knock-down), chromatin immunoprecipitation, stable isotope labeling of amino acids and quantitative mass spectrometry proteomics, immunohistochemistry and Western Blotting (Whittle et al, 2008; Boulard et al, 2010; Sporn et al, 2009; Kapoor et al, 2010; Zee et al, 2010; Hua et al, 2008).

Immunohistochemistry studies of histone variant expression in tissue samples removed at surgery or by biopsy from subjects diagnosed with lung cancer, breast cancer and melanoma have been reported. These immunohistochemistry studies report that staining of histone macroH2A (mH2A) and H2AZ variants in resected cancer tissue samples may have prognostic application in these cancers (Sporn et al, 2009, Hua et al, 2008, Kapoor et al, 2010). One disadvantage of immunohistochemical methods for clinical use is that tissue sample collection is invasive involving surgery or biopsy. Another disadvantage of immunohistochemistry methods is that they are unsuited for early diagnosis or for screening diagnostics as a reasonable expectation of the disease must usually already exist before a biopsy or tissue resection is made. Minimally invasive blood ELISA tests are suitable for a wider range of applications and would overcome these disadvantages and be preferable for the patient as well as faster, lower cost and more high-throughput for the healthcare provider.

WO 2005/019826 relates to the diagnosis of disease conditions, such as cancer and autoimmune disease, by the analysis of histone modifications associated with cell-free nucleosomes in samples from individuals. WO 2013/030579 relates to methods for detecting and measuring the presence of mono-nucleosomes and oligo-nucleosomes and nucleosomes that contain particular histone variants and the use of such measurements for the detection and diagnosis of disease.

We now describe methods for the analysis of cell free nucleosomes with respect to histone H1; including whether or not histone H1 is present in a nucleosome and, if present, its nature in terms of the variant (or isoform) present and the inclusion of any histone H1 post-translational modifications (PTMs).

SUMMARY OF THE INVENTION

According to a first aspect of the invention, there is provided a cell free nucleosome comprising a histone H1 protein or a histone H1 modification, or a histone H1 variant or isoform for use as a biomarker for the detection or diagnosis of cancer, cardiomyopathy, systemic lupus erythematosus, colitis, chronic obstructive pulmonary disorder, Crohn's disease and rheumatoid arthritis.

According to a further aspect of the invention, there is provided a method for detecting the presence of a cell free nucleosome containing histone H1 or a histone H1 modification, variant or isoform in a sample which comprises the steps of:
  (i) contacting the sample with a binding agent which binds to histone H1 or the histone H1 modification, variant or isoform;
  (ii) detecting or quantifying the binding of said binding agent to histone H1 or the histone H1 modification, variant or isoform in the sample; and
  (iii) using the presence or degree of such binding as a measure of the presence of histone H1 or the histone H1 modification, variant or isoform or nucleosomes containing histone H1 or the histone H1 modification, variant or isoform in the sample.

According to a further aspect of the invention, there is provided a method for detecting the presence of a cell free nucleosome containing histone H1 or a histone H1 modification, variant or isoform in a sample which comprises the steps of:
(i) contacting the sample with a first binding agent which binds to a non-histone H1 nucleosome epitope;
(ii) contacting the nucleosomes or sample with a second binding agent which binds to histone H1 or the histone H1 modification, variant or isoform;
(iii) detecting or quantifying the binding of said second binding agent to histone H1 or the histone H1 modification, variant or isoform in the sample; and
(iv) using the presence or degree of such binding as a measure of the presence of nucleosomes containing histone H1 or the histone H1 modification, variant or isoform in the sample.

According to a further aspect of the invention, there is provided a method for detecting the presence of a cell free nucleosome containing histone H1 or a histone H1 modification, variant or isoform in a sample which comprises the steps of:
(i) contacting the sample with a first binding agent which binds to histone H1 or the histone H1 modification, variant or isoform;
(ii) contacting the nucleosomes or sample with a second binding agent which binds to a non-histone H1 nucleosome epitope;
(iii) detecting or quantifying the binding of said second binding agent to the non-histone H1 nucleosome epitope in the sample; and
(iv) using the presence or degree of such binding as a measure of the presence of nucleosomes containing histone H1 or the histone H1 modification, variant or isoform in the sample.

According to a further aspect of the invention, there is provided a method for detecting the presence of a nucleosome containing histone H1 or a histone H1 modification, variant or isoform as defined herein, in a cell which comprises the steps of:
(i) isolating chromatin from a cell;
(ii) digesting, sonicating or otherwise breaking down the chromatin to form mono-nucleosomes and/or oligonucleosomes; and
(iii) detecting or measuring the presence of histone H1 or the histone H1 modification, variant or isoform in the said nucleosomes according to a method as defined herein.

According to a further aspect of the invention, there is provided a method for detecting the presence of a nucleosome containing histone H1 or a histone H1 modification, variant or isoform in a blood, serum or plasma sample which comprises the steps of:
(i) removing, releasing or extracting histone H1 or the histone H1 modification, variant or isoform from the nucleosome complex to produce a free histone H1 or histone H1 modification, variant or isoform moiety;
(ii) detecting or quantifying the free histone H1 or histone H1 modification, variant or isoform in the sample; and
(iii) using the presence or amount of free histone H1 or histone H1 modification, variant or isoform as a measure of the presence of nucleosomes containing the histone H1 or histone H1 modification, variant or isoform in the sample.

According to a further aspect of the invention, there is provided a method for detecting or diagnosing a disease status in an animal or a human subject which comprises the steps of:
(i) detecting or measuring cell free nucleosomes containing histone H1 or a histone H1 modification, variant or isoform in a body fluid of a subject; and
(ii) using the nucleosome associated histone H1 or nucleosome associated histone H1 modification, variant or isoform level detected to identify the disease status of the subject.

According to a further aspect of the invention, there is provided a method for assessment of an animal or a human subject for suitability for a medical treatment which comprises the steps of:
(i) detecting or measuring cell free nucleosomes containing histone H1 or a histone H1 modification, variant or isoform in a body fluid of the subject; and
(ii) using the nucleosome associated histone H1 or nucleosome associated histone H1 modification, variant or isoform level detected as a parameter for selection of a suitable treatment for the subject.

According to a further aspect of the invention, there is provided a method for monitoring a treatment of an animal or a human subject which comprises the steps of:
(i) detecting or measuring cell free nucleosomes containing histone H1 or a histone H1 modification, variant or isoform in a body fluid of the subject;
(ii) repeating the detection or measurement of cell free nucleosomes containing histone H1 or a histone H1 modification, variant or isoform in a body fluid of the subject on one or more occasions; and
(iii) using any changes in the nucleosome associated histone H1 or nucleosome associated histone H1 modification, variant or isoform level detected as a parameter for any changes in the condition of the subject.

According to a further aspect of the invention, there is provided a method for identifying a histone H1 modification, variant or isoform biomarker for detecting or diagnosing a disease status in an animal or a human subject which comprises the steps of:
(i) detecting or measuring cell free nucleosomes containing the histone H1 modification, variant or isoform in a body fluid of the subject;
(ii) detecting or measuring cell free nucleosomes containing the histone H1 modification, variant or isoform in a body fluid of a healthy subject or a control subject; and
(iii) using the difference between the levels detected in diseased and control subjects to identify whether a histone H1 modification, variant or isoform is useful as a biomarker for the disease status.

According to a further aspect of the invention, there is provided a biomarker identified by the methods as defined herein.

According to a further aspect of the invention, there is provided a kit for the detection of a cell free nucleosome associated histone H1 or histone H1 modification, variant or isoform which comprises a ligand or binder specific for histone H1 or the histone H1 modification, variant or isoform or component part thereof, or a structural/shape mimic of histone H1 or the histone H1 modification, variant or isoform or component part thereof, together with instructions for use of the kit in accordance with any one of the methods defined herein.

According to a further aspect of the invention, there is provided the use of histone H1 associated with a cell free nucleosome as a biomarker for the diagnosis of cancer, cardiomyopathy, systemic lupus erythematosus, colitis, chronic obstructive pulmonary disorder, Crohn's disease and rheumatoid arthritis.

According to a further aspect of the invention, there is provided the use of a histone H1 modification, variant or isoform associated with a cell free nucleosome as a biomarker for the diagnosis of cancer, cardiomyopathy, systemic lupus erythematosus, colitis, chronic obstructive pulmonary disorder, Crohn's disease and rheumatoid arthritis.

DETAILED DESCRIPTION OF THE INVENTION

According to a first aspect of the invention, there is provided a cell free nucleosome containing a histone H1 protein for use as a biomarker for the diagnosis of cancer, cardiomyopathy, systemic lupus erythematosus, colitis, chronic obstructive pulmonary disorder, Crohn's disease and rheumatoid arthritis.

According to a further aspect of the invention there is provided a cell free nucleosome comprising a histone H1 modification, variant or isoform for use as a biomarker for the diagnosis of cancer, cardiomyopathy, systemic lupus erythematosus, colitis, chronic obstructive pulmonary disorder, Crohn's disease and rheumatoid arthritis.

The nucleosome core consists of 8 histone proteins including a pair each of H2A, H2B, H3 and H4 histone proteins. Histone H1 (H1) is not a core histone but is located on the outside of the core and acts as a linker. In particular, H1 is involved with the packing of the "beads on a string" sub-structures into a high order structure. Without being bound by theory, the present inventors have identified that H1 associated with cell free nucleosomes originating from a tumor are subject to further modifications which leads to the presence of histone H1 modifications, variants and/or isoforms or the loss of histone H1 entirely.

The main histone H1 variants or isoforms include, without limitation, H1.0 and H1.10 which are expressed in proliferating and resting somatic cells as well as H1 variants H1.1, H1.2, H1.3, H1.4, H.1.5 and H1.6 which are expressed at high levels in dividing cells. In addition there are germ line specific variants including H1.8 which is expressed mainly in the testis and H1.7 which is expressed mainly in the oocyte. The histone variant composition of chromatin is altered in cancer cells and it is reported that, of the common H1 isoforms, histone H1.0 isoform expression is down regulated in cancer cells whereas histone isoforms H1.1, H1.2, H1.3, H1.4 and H.15 are expressed at high levels in cancer cells (Scaffidi, 2015). Therefore, in one embodiment, the histone H1 variant and/or isoform associated with a cell free nucleosome comprises at least one of the histone H1 variants and/or isoforms as listed herein.

H1 histone may be post-translationally modified at amino acid residues located in the N- and C-terminal tails as well as within the globular domain of the protein and these modifications may be associated with cancer (Izzo and Schneider, 2015). It will be understood that reference herein to "histone H1 modifications" refer to H1 post-translational modifications (PTM) which may include acetylation, methylation, which may be mono-, di-or tri-methylation, phosphorylation, ubiquitination, ADP ribosylation, citrullination, hydroxylation, glycosylation, nitrosylation, glutamination and/or isomerisation. A histone amino acid residue having a modification may be any Ser, Lys, Arg, His, Glu, Pro or Thr residue within the histone amino acid sequence.

For example, a lysine residue within the core histone sequence may be mono-, di-or tri-methylated, acetylated or ubiquitinated, an arginine residue within the core histone sequence may be monomethylated, symmetrically or asymmetrically dimethylated or converted to citrulline, a serine or threonine residue within the core histone sequence may be phosphorylated and/or a proline residue within the core sequence may be isomerised.

It will be understood by a person skilled in the art that the notation used to describe a particular histone modification indicates which histone has been modified, the particular amino acid (s) that have been modified and the type of modification that has occurred. For example, H1K64(Ac) denotes the acetylation of histone H1 at lysine 64.

In one embodiment, the biomarker comprises a histone H1 modification associated with a cell free nucleosome. In a further embodiment, the histone H1 modification is selected from phosphorylation, acetylation, methylation, ubiquitination and/or formylation. H1 modifications may include: phosphorylation at sites S2, T4, T11, S/T18, S27, T31, S36, S37, T39, S41, S44, S107, T138, T142, T146, T147, T154, T155, T165, S172, S173, T180, S/T187, S189; acetylation at sites: S2, K17, K26, K34, K46, K49, K52, K63, K64, K85, K88, K90, K93, K97, K109, K168, K169, K192, K209; methylation at sites: K26, K27, K34, K52, K64, K97, K106, K119, K148, K168, K169, K187; ubiquitination at sites: K17, K21, K34, K46, K47, K64, K65, K75, K76, K85, K86, K90, K91, K97, K98, K106, K107; formylation at sites: K17, K34, K46, K63, K64, K67, K75, K85, K88, K90, K97, K110, K140, K141, K160. Therefore, in one embodiment, the histone H1 modification associated with a cell free nucleosome comprises at least one of the histone H1 modifications as listed herein.

It will be clear to those skilled in the art that inclusion of tests for nucleosomes containing different or additional histone H1 modifications, variants or isoforms would be likely to improve the discrimination of differential diagnosis using such patterns. Therefore, in one embodiment, the biomarker comprises at least one histone H1 modification and/or variant and/or isoform associated with a cell free nucleosome.

In one embodiment, the nucleosome is a cell free mononucleosome or oligonucleosome.

According to one particular aspect of the invention which may be mentioned, there is provided the use of a histone H1 modification, variant or isoform as a biomarker for the diagnosis of cancer, cardiomyopathy, systemic lupus erythematosus, colitis, chronic obstructive pulmonary disorder, Crohn's disease and rheumatoid arthritis.

In one embodiment, the histone H1 modification, variant or isoform is used as a biomarker for cancer. In a further embodiment, the cancer is a cancer of the bladder, breast, colon, cervix, esophagus, kidney, large intestine, lung, oral cavity, ovary, pancreas, prostate, rectum, skin or stomach. In one particular embodiment which may be mentioned, the cancer is a cancer of the colon, lung, oral cavity or pancreas.

In one embodiment a histone variant that is highly expressed in cancer cells is used as the solid phase antibody in a classical double-antibody immunoassay method in conjunction with another nucleosome epitope located within the nucleosome core or associated DNA which also varies in cancer.

In another embodiment a panel of assays of the invention are used as a panel test of the disease status of a subject.

The term "biomarker" means a distinctive biological or biologically derived indicator of a process, event, or condition. Biomarkers can be used in methods of diagnosis, e.g. clinical screening, and prognosis assessment and in monitoring the results of therapy, identifying patients most likely to respond to a particular therapeutic treatment, drug screening and development. Biomarkers and uses thereof are valuable for identification of new drug treatments and for discovery of new targets for drug treatment.

Methods of Detection

According to a further aspect of the invention there is provided a method for detecting and measuring cell free nucleosomes containing histone H1 in a sample by an immunoassay which comprises the steps of:
 (i) contacting the sample with an antibody or other binder which binds to histone H1;
 (ii) detecting and/or quantifying the binding of said antibody or other binder to histone H1 in the sample; and
 (iii) using the presence or degree of such binding as a measure of the presence of a cell free nucleosome associated histone H1 in the sample.

As explained herein, it has surprisingly been found that cell free nucleosomes originating from tumor cells are more likely to have lost histone H1 histone H1 is absent). Therefore, if the detected and measured cell free nucleosomes are not associated with histone H1, then these are considered to have originated from a tumor.

According to a further aspect of the invention there is provided a method for detecting and measuring cell free nucleosomes containing specific histone H1 modifications, variants or isoforms in a sample by an immunoassay which comprises the steps of:
 (i) contacting the sample with an antibody or other binder which binds to a histone H1 modification, variant or isoform;
 (ii) detecting and/or quantifying the binding of said antibody or other binder to the histone H1 modification, variant or isoform species in the sample; and
 (iii) using the presence or degree of such binding as a measure of the presence of a cell free nucleosome associated histone H1 modification, variant or isoform in the sample.

As explained herein, where cell free nucleosomes originating from tumor cells do have histone H1 present, then that H1 is likely to be present as variants or isoforms that differ from the H1 variants present in most nucleosomes originating in healthy cells. Similarly H1 present in a cell free nucleosome originating from tumor cells are likely to contain different patterns of H1 modifications than those present in nucleosomes originating in healthy cells. Therefore, a histone H1 modification, variant, or isoform associated with a cell free nucleosomes is likely to have originated from a tumor.

According to a further aspect of the invention, there is provided a double antibody, immunometric or sandwich immunoassay method for detecting the presence of a cell free nucleosome containing histone H1 in a sample which comprises the steps of:
 (i) contacting the sample with a first binding agent which binds to nucleosomes or a non-histone H1 nucleosome epitope;
 (ii) contacting the nucleosomes or sample with a second binding agent which binds to histone H1;
 (iii) detecting or quantifying the binding of said second binding agent to histone H1 in the sample; and
 (iv) using the presence or degree of such binding as a measure of the presence of nucleosomes containing histone H1 in the sample.

According to a further aspect of the invention, there is provided a method for detecting the presence of a cell free nucleosome containing histone H1 in a sample which comprises the steps of:
 (i) contacting the sample with a first binding agent which binds to histone H1;
 (ii) contacting the nucleosomes or sample with a second binding agent which binds to nucleosomes or a non-histone H1 nucleosome epitope;
 (iii) detecting or quantifying the binding of said second binding agent to nucleosomes or the non-histone H1 nucleosome epitope in the sample; and
 (iv) using the presence or degree of such binding as a measure of the presence of nucleosomes containing histone H1 in the sample.

According to a further aspect of the invention there is provided a double antibody, immunometric or sandwich immunoassay method for detecting and measuring cell free nucleosomes containing specific histone H1 modifications, variants or isoforms in a sample. One embodiment of this aspect is an immunoassay which comprises the steps of:
 (i) contacting the sample which may contain cell free nucleosomes with a first antibody or other binder which binds to nucleosomes or a non-histone H1 nucleosome epitope;
 (ii) contacting the cell free nucleosomes or sample with a second antibody or other binder which binds to a histone H1 modification, variant or isoform;
 (iii) detecting and/or quantifying the binding of said second antibody or other binder to the histone H1 modification, variant or isoform species in the sample; and
 (iv) using the presence or degree of such binding as a measure of the presence of a cell free nucleosome associated histone H1 modification, variant or isoform in the sample.

According to another embodiment there is provided a method for detecting and measuring cell free nucleosomes containing specific histone H1 modifications, variants or isoforms in a sample by an immunoassay which comprises the steps of:
 (i) contacting the sample which may contain cell free nucleosomes with a first antibody or other binder which binds to a histone H1 modification, variant or isoform;
 (ii) contacting the cell free nucleosomes or sample with a second antibody or other binder which binds to nucleosomes or a non-histone H1 nucleosome epitope;
 (iii) detecting and/or quantifying the binding of said second antibody or other binder to nucleosomes or the non-histone H1 nucleosome epitope in the sample; and
 (iv) using the presence or degree of such binding as a measure of the presence of a cell free nucleosome associated histone H1 modification, variant or isoform in the sample.

A variety of antibodies or other binders may be employed in the invention as a binder which binds to nucleosomes. These include binders directed to bind to epitopes that occur in intact nucleosomes and not in free histones (for example; an epitope found at the junction between two histones in a nucleosome) and also binders directed to any nucleosome component including common nucleosome protein, histone or nucleic acid epitopes.

References herein to "non-histone H1 nucleosome epitope" refer to any epitope present in a nucleosome that is not present on histone H1. Such epitopes include any epitope that occurs in histone H2A, H2B, H3 or H4 or any DNA epitope. Use of a double-antibody assay wherein one antibody binds to a histone H1 epitope and the other antibody binds to a "non-histone H1 nucleosome epitope" ensures that the histone H1 epitope detected by assay is incorporated in a nucleosome.

Multiple isoforms or variants have been reported for histones H2A, H2B and H3. Histone H4 on the other hand is reported to exist as a single form (Tachiwana et al, 2011). It will be clear to those skilled in the art that an ELISA method of the invention using an antibody or binder targeted to bind to histone H4 will bind to virtually all nucleosomes in a sample. It will further be clear to those skilled in the art that suitable antibodies or ligands produced for this application may be targeted to regions of histone H4 that are not subject to PTM modification. This will further increase the universality of the selected epitope as an epitope common to all or most nucleosomes. Therefore, in one embodiment, the antibody or other binder which binds to nucleosomes is targeted to histone H4, in particular to regions of histone H4 which are not subject to PTM modification. Similarly, it will be clear to those skilled in the art that similar suitable antibodies may be targeted to bind regions of other histone moieties selected such that the regions are common to all or most histone variants or isoforms of the said histone moiety and that are not subject to PTM (for example without limitation; common regions of histones H2A, H2B or H3).

It will be clear to those skilled in the art that the methods of the invention can be used to detect and measure nucleosomes directly in any samples where they occur, for example in samples obtained by digestion of chromatin extracted from cells or in biological fluids such as blood, serum or plasma samples.

The methods of the invention are effective for the detection of all or most cancers. It will be clear to those skilled in the art that the clinical performance of the invention may be improved further by inclusion of further nucleosome structure tests and by examination of the ratios of different nucleosome structures present.

It will be clear to those skilled in the art that the methods of the invention described include a variety of embodiments including classical competitive immunoassays as well as biosensor type assays and label-free assays of the type marketed for example by ForteBio Incorporated of USA which may be immunometric in nature.

According to one embodiment of the invention there is provided a method for detecting and measuring a histone H1 modification, variant or isoform, or a cell free nucleosome associated histone H1 modification, variant or isoform, in a sample by a label-free immunometric immunoassay which comprises the steps of:
(i) contacting the sample with an antibody or other binder which binds to a histone H1 modification, variant or isoform;
(ii) detecting and/or quantifying the binding of said antibody or other binder to a histone H1 modification, variant or isoform in the sample; and
(iii) using the presence or degree of such binding as a measure of the presence of a histone H1 modification, variant or isoform or a cell free nucleosome associated histone H1 modification, variant or isoform in the sample.

According to a further embodiment of the invention there is provided a method for detecting and measuring a cell free histone H1 modification, variant or isoform, or a cell free nucleosome associated histone H1 modification, variant or isoform, in a sample by a competitive immunoassay which comprises the steps of:
(i) contacting the sample with an antibody or other binder which binds to a histone H1 modification, variant or isoform;
(ii) detecting and/or quantifying the binding of said antibody or other binder to a histone H1 modification, variant or isoform in the sample; and
(iii) using the presence or degree of such binding as a measure of the presence of a histone H1 modification, variant or isoform in the sample.

According to a further aspect of the invention there is provided a method for detecting the proportion of nucleosomes that comprises a histone H1 modification, variant or isoform in a sample comprising the steps of:
(i) detecting or measuring the level of nucleosomes in a sample;
(ii) detecting or measuring the level of a nucleosome associated histone H1 modification, variant or isoform according to a method of the invention; and
(iii) using the two measurements to determine the proportion of nucleosomes that contain the histone H1 modification, variant or isoform.

According to one embodiment of this aspect of the invention; both the total nucleosome level in the sample and the nucleosome associated histone H1 or histone H1 modification, variant or isoform level of interest are measured using the method of the invention. In another embodiment nucleosome ELISA methods of the current art are used to determine total nucleosome levels. In yet another embodiment a measure of cell free DNA is used as a proxy for total nucleosome level.

According to a further aspect of the invention there is provided a method for detecting or measuring the presence and/or the level of cell free nucleosomes containing histone H1 in a cell which comprises the steps of:
(i) isolating chromatin from a cell;
(ii) digesting, sonicating or otherwise breaking down the chromatin to form mono-nucleosomes and/or oligo-nucleosomes; and
(iii) detecting or measuring the presence of histone H1 in the mono-nucleosomes and/or oligo-nucleosomes by means of a method as described herein.

According to a further aspect of the invention there is provided a method for detecting or measuring the presence and/or the level of cell free nucleosomes containing a particular histone H1 modification, variant or isoform in a cell which comprises the steps of:
(i) isolating chromatin from a cell;
(ii) digesting, sonicating or otherwise breaking down the chromatin to form mono-nucleosomes and/or oligo-nucleosomes; and
(iii) detecting or measuring the presence of a histone H1 modification, variant or isoform in the mono-nucleosomes and/or oligo-nucleosomes by means of a method as described herein.

Methods for producing mono-nucleosomes and/or oligo-nucleosomes from chromatin are well known in the art and include enzyme digestion and sonication (Dai et al, 2011).

It will be appreciated by those skilled in the art that the described method of detecting nucleosome associated histone H1 modification, variant or isoform in cells or tissues is simpler, faster, cheaper, more quantitative and/or more reproducible than currently used methods including IHC, Western Blotting or FACS. The level, concentration or quantity of a particular nucleosome associated histone H1 modification, variant or isoform may be expressed in absolute terms or relative terms, for example as a proportion of the total nucleosomes or total DNA present or as a ratio to the level of nucleosomes containing another histone variant or PTM or nucleotide.

Anti-histone H1 antibodies for use in the invention include antibodies directed to bind to particular histone H1 variants or isoforms, antibodies directed to bind to particular histone H1 post-translational modifications and antibodies directed to bind to histone H1 per se directed to bind to common H1 epitopes that occurs in all or most H1 isoforms or variants. All of these types of antibodies are well known in the art and available commercially. Antibodies to "non-histone H1 nucleosome epitope" are directed to bind to any epitope present in a nucleosome that is not present on histone H1. Such epitopes include any epitope that occurs in histone H2A, H2B, H3 or H4 or any DNA epitope. These antibodies are also well known in the art and available commercially. It will be clear to those skilled in the art that the terms antibody, binder or ligand in regard to any aspect of the invention is not limiting but intended to include any binder capable of binding to specific molecules or entities and that any suitable binder can be used in the method of the invention. It will also be clear that the term nucleosomes is intended to include mononucleosomes and oligonucleosomes and any chromatin fragments that can be analysed in fluid media.

A further aspect of the invention provides ligands or binders, such as naturally occurring or chemically synthesised compounds, capable of specific binding to the biomarker. A ligand or binder according to the invention may comprise a peptide, an antibody or a fragment thereof, or a synthetic ligand such as a plastic antibody, or an aptamer or oligonucleotide, capable of specific binding to the biomarker. The antibody can be a monoclonal antibody or a fragment thereof capable of specific binding to the biomarker. A ligand according to the invention may be labeled with a detectable marker, such as a luminescent, fluorescent, enzyme or radioactive marker; alternatively or additionally a ligand according to the invention may be labeled with an affinity tag, e.g. a biotin, avidin, streptavidin or His (e.g. hexa-His) tag.

Alternatively ligand binding may be determined using a label-free technology for example that of ForteBio Inc.

A biosensor according to the invention may comprise the biomarker or a structural/shape mimic thereof capable of specific binding to an antibody against the biomarker. Also provided is an array comprising a ligand or mimic as described herein.

Also provided by the invention is the use of one or more ligands as described herein, which may be naturally occurring or chemically synthesised, and is suitably a peptide, antibody or fragment thereof, aptamer or oligonucleotide, or the use of a biosensor of the invention, or an array of the invention, or a kit of the invention to detect and/or quantify the biomarker. In these uses, the detection and/or quantification can be performed on a biological sample as defined herein.

Identifying and/or quantifying can be performed by any method suitable to identify the presence and/or amount of a specific protein in a biological sample from a patient or a purification or extract of a biological sample or a dilution thereof. In methods of the invention, quantifying may be performed by measuring the concentration of the biomarker in the sample or samples. Biological samples that may be tested in a method of the invention include those as defined hereinbefore. The samples can be prepared, for example where appropriate diluted or concentrated, and stored in the usual manner.

Identification and/or quantification of biomarkers may be performed by detection of the biomarker or of a fragment thereof, e.g. a fragment with C-terminal truncation, or with N-terminal truncation. Fragments are suitably greater than 4 amino acids in length, for example 5, 6, 7, 8, 9, 10, 11, 12, 13, 14, 15, 16, 17, 18, 19, or 20 amino acids in length. It is noted in particular that peptides of the same or related sequence to that of histone tails are particularly useful fragments of histone proteins.

The biomarker may be directly detected, e.g. by SELDI or MALDI-TOF. Alternatively, the biomarker may be detected directly or indirectly via interaction with a ligand or ligands such as an antibody or a biomarker-binding fragment thereof, or other peptide, or ligand, e.g. aptamer, or oligonucleotide, capable of specifically binding the biomarker. The ligand or binder may possess a detectable label, such as a luminescent, fluorescent or radioactive label, and/or an affinity tag.

For example, detecting and/or quantifying can be performed by one or more method(s) selected from the group consisting of: SELDI (-TOF), MALDI (-TOF), a 1-D gel-based analysis, a 2-D gel-based analysis, Mass spec (MS), reverse phase (RP) LC, size permeation (gel filtration), ion exchange, affinity, HPLC, UPLC and other LC or LC MS-based techniques. Appropriate LC MS techniques include ICAT® (Applied Biosystems, CA, USA), or iTRAQ® (Applied Biosystems, CA, USA). Liquid chromatography (e.g. high pressure liquid chromatography (HPLC) or low pressure liquid chromatography (LPLC)), thin-layer chromatography, NMR (nuclear magnetic resonance) spectroscopy could also be used.

Methods of diagnosing or monitoring according to the invention may comprise analysing a sample by SELDI TOF or MALDI TOF to detect the presence or level of the biomarker. These methods are also suitable for clinical screening, prognosis, monitoring the results of therapy, identifying patients most likely to respond to a particular therapeutic treatment, for drug screening and development, and identification of new targets for drug treatment.

Identifying and/or quantifying the analyte biomarkers may be performed using an immunological method, involving an antibody, or a fragment thereof capable of specific binding to the biomarker. Suitable immunological methods include sandwich immunoassays, such as sandwich ELISA, in which the detection of the analyte biomarkers is performed using two antibodies which recognize different epitopes on a analyte biomarker; radioimmunoassays (RIA), direct, indirect or competitive enzyme linked immunosorbent assays (ELISA), enzyme immunoassays (EIA), Fluorescence immunoassays (FIA), western blotting, immunoprecipitation and any particle-based immunoassay (e.g. using gold, silver, or latex particles, magnetic particles, or Q-dots). Immunological methods may be performed, for example, in microtitre plate or strip format.

The immunoassays of the invention include immunometric assays employing enzyme detection methods (for example ELISA), fluorescence labelled immunometric assays, time-resolved fluorescence labelled immunometric assays, chemiluminescent immunometric assays, immunoturbidimetric assays, particulate labelled immunometric assays and immunoradiometric assays and competitive immunoassay methods including labelled antigen and labelled antibody competitive immunoassay methods with a variety of label types including radioactive, enzyme, fluorescent, time-resolved fluorescent and particulate labels. All of said immunoassay methods are well known in the art, see for example Salgame et al, 1997 and van Nieuwenhuijze et al, 2003.

The identification of key biomarkers specific to a disease is central to integration of diagnostic procedures and therapeutic regimes. Using predictive biomarkers appropriate diagnostic tools such as biosensors can be developed; accordingly, in methods and uses of the invention, identifying and quantifying can be performed using a biosensor, microanalytical system, microengineered system, microseparation system, immunochromatography system or other suitable analytical devices. The biosensor may incorporate an immunological method for detection of the biomarker(s), electrical, thermal, magnetic, optical (e.g. hologram) or acoustic technologies. Using such biosensors, it is possible to detect the target biomarker(s) at the anticipated concentrations found in biological samples.

As used herein, the term "biosensor" means anything capable of detecting the presence of the biomarker. Examples of biosensors are described herein.

Biosensors according to the invention may comprise a ligand binder or ligands, as described herein, capable of specific binding to the biomarker. Such biosensors are useful in detecting and/or quantifying a biomarker of the invention.

The biomarker(s) of the invention can be detected using a biosensor incorporating technologies based on "smart" holograms, or high frequency acoustic systems, such systems are particularly amenable to "bar code" or array configurations.

In smart hologram sensors (Smart Holograms Ltd, Cambridge, UK), a holographic image is stored in a thin polymer film that is sensitised to react specifically with the biomarker. On exposure, the biomarker reacts with the polymer leading to an alteration in the image displayed by the hologram. The test result read-out can be a change in the optical brightness, image, colour and/or position of the image. For qualitative and semi-quantitative applications, a sensor hologram can be read by eye, thus removing the need for detection equipment. A simple colour sensor can be used to read the signal when quantitative measurements are required. Opacity or colour of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Suitably, biosensors for detection of one or more biomarkers of the invention combine biomolecular recognition with appropriate means to convert detection of the presence, or quantitation, of the biomarker in the sample into a signal. Biosensors can be adapted for "alternate site" diagnostic testing, e.g. in the ward, outpatients' department, surgery, home, field and workplace.

Biosensors to detect one or more biomarkers of the invention include acoustic, plasmon resonance, holographic, Bio-Layer Interferometry (BLI) and microengineered sensors. Imprinted recognition elements, thin film transistor technology, magnetic acoustic resonator devices and other novel acousto-electrical systems may be employed in biosensors for detection of the one or more biomarkers of the invention.

Methods involving identification and/or quantification of one or more biomarkers of the invention can be performed on bench-top instruments, or can be incorporated onto disposable, diagnostic or monitoring platforms that can be used in a non-laboratory environment, e.g. in the physician's office or at the patient's bedside.

Suitable biosensors for performing methods of the invention include "credit" cards with optical or acoustic readers. Biosensors can be configured to allow the data collected to be electronically transmitted to the physician for interpretation and thus can form the basis for e-medicine.

Methods of Diagnosis

According to a further aspect of the invention, there is provided a method for detecting or diagnosing a disease status in an animal or a human subject which comprises the steps of:
(i) detecting or measuring cell free nucleosomes containing histone H1 in a body fluid of a subject; and
(ii) using the nucleosome associated histone H1 level detected to identify the disease status of the subject.

According to a further aspect of the invention, there is provided a method for detecting or diagnosing a disease status in an animal or a human subject which comprises the steps of:
(i) detecting or measuring cell free nucleosomes containing a histone H1 modification, variant or isoform in a body fluid of a subject; and
(ii) using the nucleosome associated histone H1 modification, variant or isoform level detected to identify the disease status of the subject.

According to another aspect of the invention there is provided a method for detecting or diagnosing the presence of a disease by measuring or detecting the presence and/or the level or concentration of cell free nucleosomes containing histone H1 or a histone H1 modification, variant or isoform in a body fluid, and using the detected level as a biomarker of the disease status of a subject including, without limitation, a clinical diagnosis of a disease, a differential diagnosis of disease type or subtype, or a disease prognosis, or a disease relapse, or a diagnosis of subject susceptibility to treatment regimens. It will be appreciated by those skilled in the art that body fluids used for diagnostic testing include without limitation blood, serum, plasma, urine, cerebrospinal fluid, sputum, feces and other fluids. In a preferred embodiment the body fluid selected as the sample is blood, serum or plasma. The assay response level, concentration or quantity of nucleosome associated histone H1 or a nucleosome associated histone H1 modification, variant or isoform in a body fluid may be expressed in absolute terms or relative terms, for example, without limitation, as a proportion of the total nucleosome or total DNA level present or as a ratio to the level of nucleosomes containing another histone variant or nucleotide or PTM.

In one embodiment, the cell free nucleosome associated histone H1 or histone H1 modification, variant or isoform is detected or measured as one of a panel of measurements.

In one embodiment of the invention a control sample is provided and the cut-off level for the assay to distinguish between positive or negative results is defined in relation to the result for the control sample. This could be any proportion equal to above or below the level of the control sample result. Patient results below this level are considered negative and patient results above this level are considered positive. There may also be a "grey area" range of patient results very close to the cut-off level for which the decision is considered indeterminate and/or the test should be repeated.

It will be clear to those skilled in the art that cell free nucleosomes containing histone H1 or a histone H1 modification, variant or isoform can also be detected in a biological fluid including blood, plasma, serum and urine by a procedure involving the extraction of histone H1 or the histone H1 modification, variant or isoform protein from the nucleosome complex followed by a method for the detection or quantification of the extracted free histone H1 or histone H1 modification, variant or isoform protein. Suitable extraction procedures include commonly used acid extraction procedures for histones which utilise the basic nature of histones proteins. The detection of the free histone H1 or histone H1 modification, variant or isoform may be performed, for example, by an immunoassay for the free histone moiety. Thus in one embodiment of the invention histone H1 or a histone H1 modification, variant or isoform is extracted from a biological fluid including blood, plasma, serum and urine and the extract is tested for the presence of a histone H1 modification, variant or isoform.

It is known in the art that one may detect the presence of a protein that is comprised as part of a complex containing other moieties by immunoassay methods. It will be clear to those skilled in the art that cell free nucleosomes containing histone H1 or a histone H1 modification, variant or isoform can be detected in a biological fluid including blood, plasma, serum and urine by a procedure involving the direct immunoassay of the histone, modification, isoform or variant itself in the fluid. In this procedure a single antibody immunoassay, utilising an antibody directed to an epitope present on a histone, modification, isoform or variant, or a 2-site immunoassay, utilising two antibodies directed to two epitopes present on histone H1 or a histone H1 modification, variant or isoform, is used to detect the presence of histone H1 or a histone H1 modification, variant or isoform within a nucleosome. Thus in another embodiment of the invention histone H1 or a histone H1 modification, variant or isoform contained within a nucleosome is detected directly in a biological fluid including blood, plasma, serum, sputum, feces and urine by use of an immunoassay method.

Thus in one embodiment of the invention histone H1 or a histone H1 modification, variant or isoform is extracted from a biological fluid including blood, plasma, serum, sputum, feces and urine and the extract is tested.

The terms "detecting" and "diagnosing" as used herein encompass identification, confirmation, and/or characterisation of a disease state. Methods of detecting, monitoring and of diagnosis according to the invention are useful to confirm the existence of a disease, to monitor development of the disease by assessing onset and progression, or to assess amelioration or regression of the disease. Methods of detecting, monitoring and of diagnosis are also useful in methods for assessment of clinical screening, prognosis, choice of therapy, evaluation of therapeutic benefit, i.e. for drug screening and drug development.

Efficient diagnosis and monitoring methods provide very powerful "patient solutions" with the potential for improved prognosis, by establishing the correct diagnosis, allowing rapid identification of the most appropriate treatment (thus lessening unnecessary exposure to harmful drug side effects), and reducing relapse rates.

In one embodiment, said biomarker is released from the cells of a tumour. Thus, according to a further aspect of the invention there is provided a method for the detection of a tumour growth which comprises the steps of (i) measuring a biomarker in a biological sample that is associated with or released from the cells of a tumour and (ii) demonstrating that the level of said biomarker is associated with the size, stage, aggressiveness or dissemination of the tumour.

It is known that increased cell turnover, cell death and apoptosis lead to increased circulatory levels of cell free nucleosomes (Holdenrieder et al, 2001). Circulating cell free nucleosomes level is a non-specific indicator and occurs in a variety of conditions including inflammatory diseases, a large variety of benign and malignant conditions, autoimmune diseases, as well as following trauma or ischaemia (Holdenrieder et al 2001). It will be clear to those skilled in the art that the invention will have application in a variety of disease areas where circulating nucleosomes have been found in subjects. These include, without limitation, trauma (for example; severe injury or surgery), extreme exercise (for example running a marathon), stroke and heart attack and sepsis or other serious infection.

In one embodiment, the method of the invention is repeated on multiple occasions. This embodiment provides the advantage of allowing the detection results to be monitored over a time period. Such an arrangement will provide the benefit of monitoring or assessing the efficacy of treatment of a disease state. Such monitoring methods of the invention can be used to monitor onset, progression, stabilisation, amelioration, relapse and/or remission.

Thus, the invention also provides a method of monitoring efficacy of a therapy for a disease state in a subject, suspected of having such a disease, comprising detecting and/or quantifying the biomarker present in a biological sample from said subject. In monitoring methods, test samples may be taken on two or more occasions. The method may further comprise comparing the level of the biomarker(s) present in the test sample with one or more control(s) and/or with one or more previous test sample(s) taken earlier from the same test subject, e.g. prior to commencement of therapy, and/or from the same test subject at an earlier stage of therapy. The method may comprise detecting a change in the nature or amount of the biomarker(s) in test samples taken on different occasions.

Thus, according to a further aspect of the invention, there is provided a method for assessment of an animal or a human subject for suitability for a medical treatment which comprises the steps of:
(i) detecting or measuring cell free nucleosomes containing histone H1 in a body fluid of the subject; and
(ii) using the nucleosome associated histone H1 level detected as a parameter for selection of a suitable treatment for the subject.

According to a further aspect of the invention, there is provided a method for assessment of an animal or a human subject for suitability for a medical treatment which comprises the steps of:
(i) detecting or measuring cell free nucleosomes containing a histone H1 modification, variant or isoform in a body fluid of the subject; and
(ii) using the nucleosome associated histone H1 modification, variant or isoform level detected as a parameter for selection of a suitable treatment for the subject.

According to a further aspect of the invention, there is provided a method for monitoring a treatment of an animal or a human subject which comprises the steps of:
(i) detecting or measuring cell free nucleosomes containing histone H1 in a body fluid of the subject;
(ii) repeating the detection or measurement of cell free nucleosomes containing histone H1 in a body fluid of the subject on one or more occasions; and
(iii) using any changes in the nucleosome associated histone H1 level detected as a parameter for any changes in the condition of the subject.

According to a further aspect of the invention, there is provided a method for monitoring a treatment of an animal or a human subject which comprises the steps of:
(i) detecting or measuring cell free nucleosomes containing a histone H1 modification, variant or isoform in a body fluid of the subject;
(ii) repeating the detection or measurement of cell free nucleosomes containing a histone H1 modification, variant or isoform in a body fluid of the subject on one or more occasions; and (iii) using any changes in the nucleosome associated histone H1 modification, variant or isoform level detected as a parameter for any changes in the condition of the subject.

According to a further aspect of the invention, there is provided a method for monitoring efficacy of therapy for a disease state in a human or animal subject, comprising:
(i) quantifying the amount of the biomarker as defined herein (i.e. histone H1 or a histone H1 modification, variant or isoform); and
(ii) comparing the amount of said biomarker in a test sample with the amount present in one or more control(s) and/or one or more previous test sample(s) taken at an earlier time from the same test subject.

It will be understood that references to "biomarker" as described herein as referring to histone H1 itself or a histone H1 modification, variant or isoform.

A change in the level of the biomarker in the test sample relative to the level in a previous test sample taken earlier from the same test subject may be indicative of a beneficial effect, e.g. stabilisation or improvement, of said therapy on the disorder or suspected disorder. Furthermore, once treatment has been completed, the method of the invention may be periodically repeated in order to monitor for the recurrence of a disease.

Methods for monitoring efficacy of a therapy can be used to monitor the therapeutic effectiveness of existing therapies and new therapies in human subjects and in non-human animals (e.g. in animal models). These monitoring methods can be incorporated into screens for new drug substances and combinations of substances.

In a further embodiment the monitoring of more rapid changes due to fast acting therapies may be conducted at shorter intervals of hours or days.

Diagnostic kits for the diagnosis and monitoring of the presence of a disease state are described herein. In one embodiment, the kits additionally contain a biosensor capable of identifying and/or quantifying a biomarker. Suitably a kit according to the invention may contain one or more components selected from the group: a ligand binder, or ligands, specific for the biomarker or a structural/shape mimic of the biomarker, one or more controls, one or more reagents and one or more consumables; optionally together with instructions for use of the kit in accordance with any of the methods defined herein.

The identification of biomarkers for a disease state permits integration of diagnostic procedures and therapeutic regimes. Detection of a biomarker of the invention can be used to screen subjects prior to their participation in clinical trials. The biomarkers provide the means to indicate therapeutic response, failure to respond, unfavourable side-effect profile, degree of medication compliance and achievement of adequate serum drug levels. The biomarkers may be used to provide warning of adverse drug response. Biomarkers are useful in development of personalized therapies, as assessment of response can be used to fine-tune dosage, minimise the number of prescribed medications, reduce the delay in attaining effective therapy and avoid adverse drug reactions. Thus by monitoring a biomarker of the invention, patient care can be tailored precisely to match the needs determined by the disorder and the pharmacogenomic profile of the patient, the biomarker can thus be used to titrate the optimal dose, predict a positive therapeutic response and identify those patients at high risk of severe side effects.

Biomarker-based tests provide a first line assessment of 'new' patients, and provide objective measures for accurate and rapid diagnosis, not achievable using the current measures.

Furthermore, diagnostic biomarker tests are useful to identify family members or patients with mild or asymptomatic disease or who may be at high risk of developing symptomatic disease. This permits initiation of appropriate therapy, or preventive measures, e.g. managing risk factors. These approaches are recognised to improve outcome and may prevent overt onset of the disorder.

Biomarker monitoring methods, biosensors and kits are also vital as patient monitoring tools, to enable the physician to determine whether relapse is due to worsening of the disorder. If pharmacological treatment is assessed to be inadequate, then therapy can be reinstated or increased; a change in therapy can be given if appropriate. As the biomarkers are sensitive to the state of the disorder, they provide an indication of the impact of drug therapy.

Biomarkers for detecting the presence of a disease are essential targets for discovery of novel targets and drug molecules that retard or halt progression of the disorder. As the level of the biomarker is indicative of disorder and of drug response, the biomarker is useful for identification of novel therapeutic compounds in in vitro and/or in vivo assays. Biomarkers of the invention can be employed in methods for screening for compounds that modulate the activity of the biomarker.

Thus, in a further aspect of the invention, there is provided the use of a binder or ligand, as described, which can be a peptide, antibody or fragment thereof or aptamer or oligonucleotide according to the invention; or the use of a biosensor according to the invention, or an array according to the invention; or a kit according to the invention, to identify a substance capable of promoting and/or of suppressing the generation of the biomarker.

Also there is provided a method of identifying a substance capable of promoting or suppressing the generation of the biomarker in a subject, comprising administering a test substance to a subject animal and detecting and/or quantifying the level of the biomarker present in a test sample from the subject.

Methods of Treatment

According to a further aspect of the invention, there is provided a method of treating a disease selected from: cancer, cardiomyopathy, systemic lupus erythematosus, colitis, chronic obstructive pulmonary disorder, Crohn's disease and rheumatoid arthritis, in an animal or a human subject, which comprises the following steps:
(i) detecting or measuring cell free nucleosomes containing a histone H1 modification, variant or isoform in a body fluid of a subject;
(ii) using the nucleosome associated histone H1 modification, variant or isoform level detected to identify the disease status of the subject; and
(iii) treating surgically or administering a therapeutic agent to a subject diagnosed in step (ii) as a patient having said disease.

The methods described herein may further comprise comparing the level of the biomarker(s) present in the biological sample with one or more control(s). In one embodiment, the biological sample from the one or more control(s) is taken from healthy (or "normal") patient(s) and/or patient(s) with an associated benign disease. In a further embodiment, the biological sample from the one or more control(s) is taken from healthy patient(s).

Therefore, according to a further aspect of the invention, there is provided a method of treating a disease in an individual in need thereof, which comprises the step of administering a therapeutic agent to a patient identified as having differing levels of the biomarker(s) as defined herein in a biological sample when compared to the levels of said biomarker(s) in a biological sample obtained from a control subject.

In one embodiment, the disease is cancer. In a further embodiment, the cancer is selected from: breast, bladder, colorectal, skin (such as melanoma), ovarian, prostate, lung, pancreatic, bowel, liver, endometrial, lymphoma, oral, head and neck cancer, leukaemia and osteosarcoma.

Therapeutic agents and methods of surgery used for treating said diseases are well known to a person skilled in the art. Methods of treatment for cancer include, but are not limited to, surgery, chemotherapy, radiotherapy or other therapeutic agents (such as drugs or biological therapies, such as monoclonal antibodies).

Methods of Identifying Biomarkers

According to a further aspect of the invention, there is provided a method for identifying a biomarker for detecting the presence of a disease state. The term "identifying" as used herein means confirming the presence of the biomarker present in the biological sample. Quantifying the amount of the biomarker present in a sample may include determining the concentration of the biomarker present in the sample. Identifying and/or quantifying may be performed directly on the sample, or indirectly on an extract therefrom, or on a dilution thereof.

According to another aspect of the invention there is provided a method for identifying a histone H1 modification, variant or isoform biomarker for detecting or diagnosing disease status in animals or humans which comprises the steps of:
(i) detecting or measuring the level of cell free nucleosomes containing a histone H1 modification, variant or isoform in a body fluid of diseased subjects;
(ii) detecting or measuring the level of cell free nucleosomes containing a histone H1 modification, variant or isoform in a body fluid of control subjects; and
(iii) using the difference between the levels detected in diseased and control subjects to identify whether a particular histone H1 modification, variant or isoform is useful as a biomarker for that disease.

It will be clear to those skilled in the art that the control subjects may be selected on a variety of basis which may include, for example, subjects known to be free of the disease or may be subjects with a different disease (for example; for the investigation of differential diagnosis).

According to a further aspect of the invention there is provided a method for identifying a histone H1 modification, variant or isoform biomarker for assessing the prognosis of a diseased animal or human subject which comprises the steps of:
(i) detecting or measuring the level of cell free nucleosomes containing a histone H1 modification, variant or isoform in a body fluid of diseased subjects; and
(ii) correlating the level of cell free nucleosomes containing a histone H1 modification, variant or isoform detected in a body fluid of diseased subjects with the disease outcome of the subjects.

According to a further aspect of the invention there is provided a method for identifying a histone H1 modification, variant or isoform biomarker to be used for the selection of a treatment regimen for a diseased animal or human subject in need of treatment which comprises the steps of:
(i) detecting or measuring the level of cell free nucleosomes containing a histone H1 modification, variant or isoform in a body fluid of diseased subjects; and
(ii) correlating the level of cell free nucleosomes containing a histone H1 modification, variant or isoform detected in a body fluid of diseased subjects with the observed efficacy of a treatment regimen in those subjects.

According to a further aspect of the invention there is provided a method for identifying a histone H1 modification, variant or isoform biomarker to be used for monitoring the treatment of a diseased animal or human subject which comprises the steps of:
(i) detecting or measuring the level of cell free nucleosomes containing a histone H1 modification, variant or isoform in a body fluid of a diseased subject;
(ii) repeating said detection or measurement on one or more occasions during the disease progression of the subject; and
(iii) correlating the level of cell free nucleosomes containing a histone H1 modification, variant or isoform detected in a body fluid of a diseased subject with the disease progression in the subject.

According to a further aspect of the invention, there is provided a biomarker identified by the methods as defined herein.

Kits

According to a further aspect of the invention there is provided a kit for detecting or measuring cell free nucleosomes containing histone H1 which comprises a ligand or binder specific for histone H1 or a component part thereof, or a structural/shape mimic of the nucleosome or component part thereof, together with instructions for use of the kit in accordance with any of the methods defined herein.

According to a further aspect of the invention there is provided a kit for detecting or measuring cell free nucleosomes containing a particular histone H1 modification, variant or isoform which comprises a ligand or binder specific for the histone H1 modification, variant or isoform or a component part thereof, or a structural/shape mimic of the nucleosome or component part thereof, together with instructions for use of the kit in accordance with any of the methods defined herein.

Diagnostic or monitoring kits are provided for performing methods of the invention. Such kits will suitably comprise a ligand according to the invention, for detection and/or quantification of the biomarker, and/or a biosensor, and/or an array as described herein, optionally together with instructions for use of the kit.

A further aspect of the invention is a kit for detecting the presence of a disease state, comprising a biosensor capable of detecting and/or quantifying one or more of the biomarkers as defined herein.

It will be understood that the embodiments described herein may be applied to all aspects of the invention, Furthermore, all publications, including but not limited to patents and patent applications, cited in this specification are herein incorporated by reference as though fully set forth.

The invention will now be illustrated with reference to the following non-limiting examples.

Example 1

A human blood sample containing cell free nucleosomes is serially diluted and assayed for the presence of cell free nucleosomes containing histone H1 in addition to core histones. The assay method is as follows: An anti-histone H1 capture antibody directed to bind to a common H1 epitope that occurs in all or most H1 variants is diluted in 0.1M phosphate buffer pH 7.4 and added to microtitre wells (100 µL/well) and incubated overnight at 4° C. to coat the wells with capture antibody. Excess anti-histone H1 antibody is decanted. A solution of bovine serum albumin (20 g/L) is added to the wells (150 µL/well) and incubated 60 minutes at room temperature to block excess protein binding sites on the wells. Excess bovine serum albumin solution is decanted and the wells are washed twice with wash buffer (200 µL/well, 0.05M TRIS/HCl buffer pH 7.5 containing 1% Tween 20). Sample (10 µL/well) and assay buffer (50 µL/well, 0.05M TRIS/HCl pH 7.5 containing 0.9% NaCl, 0.05% sodium deoxycholate and 1% Nonidet P40 substitute) are added to the wells and incubated 90 minutes at room temperature with mild agitation. The sample and assay buffer mixture is decanted and the wells are washed three times with wash buffer (200 µL/well). A solution of labelled detection antibody directed bind to any nucleosome core epitope or a DNA epitope is added (50 µL/well) and incubated 90 minutes at room temperature with mild agitation. Excess detection antibody is decanted and the wells are again washed three times with wash buffer (200 µL/well). A solution containing a streptavidin-horse radish peroxidase conjugate is added (50 µL/well) and incubated 30 minutes at room temperature with mild agitation. Excess conjugate is decanted and the wells are again washed three times with wash buffer (200 µL/well). A coloured substrate solution (100 µL/well, 2,2'-Azinobis [3-ethylbenzothiazoline-6-sulfonic acid]-diammonium salt) is added and incubated 30 minutes at room temperature with mild agitation. A STOP solution (100 µL/well) containing 1% sodium dodecyl sulphate is added and the optical density (OD) of the wells is measured at a wavelength of 405 nm using a standard microtitre plate reader. A reproducible dose response curve of increasing colour with increasing nucleosome associated histone H1 concentration is observed with a low background signal observed in the absence of nucleosome associated histone H1. The positive ELISA signal indicates that the histone H1 detected by the ELISA is incorporated within a cell free nucleosome.

Example 2

A human blood sample containing cell free nucleosomes is serially diluted and assayed for the presence of cell free nucleosomes containing histone H1 in addition to core histones. The assay method is similar to that described in EXAMPLE 1 but utilizes a capture antibody directed bind to any nucleosome core epitope or a DNA epitope and a labelled detection antibody directed to bind to a common H1 epitope that occurs in all or most H1 variants.

Example 3

A human serum or plasma sample containing cell free nucleosomes is assayed for the presence of cell free nucleosomes containing a post-translationally modified histone H1 in addition to core histones. The assay method is similar to that described in EXAMPLE 1 but utilizes a capture antibody directed bind to any nucleosome core epitope or a DNA epitope and a labelled detection antibody directed to bind to a H1 PTM epitope (for example a histone H1 molecule which includes an amino acid residue which has been modified by acetylation, mono-, di-or tri-methylation, phosphorylation, ubiquitination, ADP ribosylation, citrullination, hydroxylation, glycosylation, nitrosylation, glutamination and/or isomerisation).

Example 4

A human blood sample containing cell free nucleosomes is assayed for the presence of cell free nucleosomes containing a post-translationally modified histone H1 in addition to core histones. The assay method is similar to that described in EXAMPLE 3 but utilizes a capture antibody directed bind to a H1 PTM epitope and a labelled detection antibody directed to bind to any nucleosome core epitope or a DNA epitope.

Example 5

A human serum or plasma sample containing cell free nucleosomes is assayed for the presence of cell free nucleosomes containing a histone H1 variant in addition to core histones. The assay method is similar to that described in EXAMPLE 1 but utilizes a capture antibody directed bind to any nucleosome core epitope or a DNA epitope and a labelled detection antibody directed to bind to an epitope specific to histone H1 variant H1.0, H1.1, H1.2, H1.3, H1.4, H1.5, H1.6, H1.7, H1.8 or histone variant H1.10.

Example 6

A human blood sample containing cell free nucleosomes is assayed for the presence of cell free nucleosomes containing a histone H1 variant in addition to core histones. The assay method is similar to that described in EXAMPLE 5 but utilizes a capture antibody directed bind to bind to an epitope specific to histone H1 variant H1.0, H1.1, H1.2, H1.3, H1.4, H1.5, H1.6, H1.7, H1.8 or histone variant H1.10 and a labelled detection antibody directed to bind to any nucleosome core epitope or a DNA epitope.

Example 7

A human serum or plasma sample containing cell free nucleosomes is assayed for the presence of cell free nucleosome adducts containing a histone H1 molecule and an adducted protein in addition to core histones. The assay method is similar to that described in EXAMPLE 1 but utilizes a capture antibody directed bind to any histone H1 epitope and labelled detection antibody directed to bind to a protein adducted to a nucleosome (for example an antibody directed to bind specifically to a High Mobility Group protein (such as HMGB1), a polycomb protein, a chromatin modification enzyme, a DNA modification enzyme, a transcription factor, an architectural or structural protein, a transcription enhancement factor, a transcription repression factor, a replication protein, a DNA damage repair protein or a nuclear hormone receptor (such as an estrogen receptor, androgen receptor, vitamin D or retinoic acid receptor or thyroid receptor molecule).

Example 8

A human serum or plasma sample containing cell free nucleosomes is assayed for the presence of cell free nucleosome adducts containing a histone H1 molecule and an adducted protein in addition to core histones. The assay method is similar to that described in EXAMPLE 7 but utilizes a capture antibody directed bind to a protein adducted to a nucleosome and a labelled detection antibody directed to bind to any histone H1 epitope.

REFERENCES

Allen et al, (2004) Nucleic Acids Research 32(3): e38
Boulard et al, (2010) Epigenetics & Chromatin 3(8): 1-13
Cell Biolabs, Inc. Product Manual for "Global DNA Methylation ELISA Kit (5'-methyl-2'-deoxycytidine Quantitation", (2011)
Dai et al, (2011) J Vis Exp. 50
Deligezer et al, (2008) Clinical Chemistry 54(7): 1125-1131
Epigentek Group Inc, Methylamp™ Global DNA Methylation Quantification Kit, User Guide, Version 2.0802, (2009)
Esteller, (2007) Nature Reviews Genetics 8: 286-298
Feinberg and Vogelstein, (1983) Nature 301: 89-92
Grutzmann et al, (2008) PLoS ONE 3(11): e3759
Hervouet et al, (2010) PLoS ONE 5(6): e11333
Hua et al, (2008) Molecular Systems Biology 4; Article number 188
Herranz and Esteller, (2007) Methods Mol Biol. 361: 25-62
Holdenrieder et al, (2001) Int. J. Cancer (Pred. Oncol.) 95: 114-120
Holdenrieder et al, (2001) Clin Chem Lab Med 39(7): 596-605
Holdenrieder et al, (2005) Clinical Chemistry 51(8): 1544-1546
Holdenreider and Stieber, (2009) Critical Reviews in Clinical Laboratory Sciences 46(1): 1-24
Izzo and Schneider, (2015) Biochimica et Biophysica Acta S1874-9399 (15) 189-3
Kapoor et al, (2010) Nature 468: 1105-1111
Mansour et al, (2010) PLoS ONE 5(12): e15585
Moore et al, (2008) The Lancet Oncology 9(4): 359-366
Ogoshi et al, (2011) Genomics 98(4): 280-7
Pennings et al, (2005) Briefings in functional genomics and proteomics 3(4): 351-361
Rodriguez-Paredes and Esteller, (2011) Nature Medicine 17(3): 330-339
Salgame et al, (1997) Nucleic Acids Research 25(3): 680-681
Scaffidi, (2015) BBA—Gene Reg. Mechanisms: doi: 10.1016/j.bbagrm.2015.09.008Sporn et al, (2009) Oncogene 28(38): 3423-8
Stroud et al, (2011) Genome Biology 12: R54
Tachiwana et al, (2011) Acta Cryst. D67: 578-583
Ting Hsiung et al, (2007) Cancer Epidemiology,Biomarkers & Prevention 16(1): 108-114
van Nieuwenhuijze et al, (2003) Ann Rheum Dis 62: 10-14
Vasser et al, (2009) Genetic Engineering and Biotechnology News, 29(7)
Whittle et al, (2008) PLoS Genet 4(9): 1-17
Zee et al, (2010) Epigenetics & Chromatin 3(22): 1-11
Zhang et al, (2011) Analytical Biochemistry 413(2): 164-170

The invention claimed is:

1. A method for detecting the presence of a cell free nucleosome containing histone H1 or a histone H1 modification, variant or isoform in a sample which comprises the steps of:
   (i) contacting the sample with a first binding agent which binds to a non-histone H1 nucleosome epitope;
   (ii) contacting the nucleosomes or sample with a second binding agent which binds to histone H1 or the histone H1 modification, variant or isoform;
   (iii) detecting or quantifying the binding of said second binding agent to histone H1 or the histone H1 modification, variant or isoform in the sample; and
   (iv) using the presence or degree of binding of said second binding agent as a measure of the presence of nucleosomes containing histone H1 or the histone H1 modification, variant or isoform in the sample.

2. A method for detecting the presence of a cell free nucleosome containing histone H1 or a histone H1 modification, variant or isoform in a sample which comprises the steps of:
   (i) contacting the sample with a first binding agent which binds to histone H1 or the histone H1 modification, variant or isoform;
   (ii) contacting the nucleosomes or sample with a second binding agent which binds to a non-histone H1 nucleosome epitope;
   (iii) detecting or quantifying the binding of said second binding agent to the non-histone H1 nucleosome epitope in the sample; and
   (iv) using the presence or degree of binding of said second binding agent as a measure of the presence of nucleosomes containing histone H1 or the histone H1 modification, variant or isoform in the sample.

3. A method as defined in claim 1, wherein the binding agent is an antibody.

4. A method according to claim 1, wherein the sample is a body fluid.

5. A method according to claim 1, wherein the sample is blood, serum or plasma.

6. The method according to claim 2, wherein the binding agent is an antibody.

7. The method according to claim 2, wherein the sample is a body fluid.

8. The method according to claim 2, wherein the sample is blood, serum or plasma.

* * * * *